US006972075B2

(12) United States Patent
Luyken et al.

(10) Patent No.: US 6,972,075 B2
(45) Date of Patent: Dec. 6, 2005

(54) METHOD FOR REMOVING 6-AMINOCAPRONITRILE FROM MIXTURES THAT CONTAIN 6-AMINOCAPRONITRILE, ADIPODINITRILE AND HEXAMETHYLENEDIAMINE

(75) Inventors: Hermann Luyken, Ludwigshafen (DE); Frank Ohlbach, Dossenheim (DE); Rolf-Hartmuth Fischer, Heidelberg (DE); Johann-Peter Melder, Böhl-Iggelheim (DE); Peter Bassler, Viernheim (DE); Andreas Ansmann, Wiesloch (DE); Günther Achhammer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 394 days.

(21) Appl. No.: 10/311,376

(22) PCT Filed: Jun. 13, 2001

(86) PCT No.: PCT/EP01/06688

§ 371 (c)(1),
(2), (4) Date: Dec. 16, 2002

(87) PCT Pub. No.: WO01/98261

PCT Pub. Date: Dec. 27, 2001

(65) Prior Publication Data

US 2004/0015004 A1 Jan. 22, 2004

(30) Foreign Application Priority Data

Jun. 19, 2000 (DE) .................. 100 29 187

(51) Int. Cl.$^7$ .................. B01D 3/14; C07C 253/34; C07C 255/24
(52) U.S. Cl. .................. 203/75; 203/77; 203/78; 203/80; 203/99; 203/DIG. 19; 558/452; 564/511

(58) Field of Search .................. 203/75, 77, 78, 203/80, 99, DIG. 19; 558/452, 454; 564/511, 564/497

(56) References Cited

U.S. PATENT DOCUMENTS

| 5,717,090 | A | * | 2/1998 | Bassler et al. | 540/539 |
| 6,139,693 | A | * | 10/2000 | Bassler et al. | 203/49 |
| 6,147,208 | A | | 11/2000 | Achhamer et al. | 540/538 |
| 6,252,115 | B1 | * | 6/2001 | Luyken et al. | 564/437 |
| 6,462,220 | B1 | * | 10/2002 | Luyken et al. | 558/459 |
| 6,599,398 | B1 | * | 7/2003 | Ostermaier et al. | 203/74 |
| 6,627,046 | B1 | * | 9/2003 | Fergusson et al. | 203/29 |
| 6,887,352 | B2 | * | 5/2005 | Ostermaier | 203/2 |

FOREIGN PATENT DOCUMENTS

| WO | WO 96/20931 | 7/1996 |
| WO | WO 97/23454 | 7/1997 |

* cited by examiner

Primary Examiner—Virginia Manoharan
(74) Attorney, Agent, or Firm—Novak Druce & Quigg

(57) ABSTRACT

The invention relates to a method for removing, by distillation, 6-aminocapronitrile from mixtures that contain 6-aminocapronitrile, adipodinitrile and hexamethylenediamine, by a) removing the hexamethylenediamine from the mixture while obtaining a mixture (I) that has a hexamethylenediamine content of less than 1 wt. -%, b) removing completely or partially the 6-aminocapronitrile from mixture (I) while obtaining a mixture (II) whose content in substances that have a higher boiling point as 6-aminocapronitrile under distillation conditions and that cannot be formed by dimerization reactions when 6-aminocapronitrile is thermally treated is less than 1 wt. -%, and c) completely or partially removing from mixture (II) the hexamethylenediamine that might be present while obtaining a mixture (IV) whose hexamethylenediamine content is higher than that of mixture (II), and a mixture (V) whose hexamethylenediamine content is lower than that of mixture (II).

8 Claims, 3 Drawing Sheets

METHOD FOR REMOVING 6-AMINOCAPRONITRILE FROM MIXTURES THAT CONTAIN 6-AMINOCAPRONITRILE, ADIPODINITRILE AND HEXAMETHYLENEDIAMINE

The present invention relates to a process for the distillative separation of 6-aminocapronitrile from mixtures containing 6-aminocapronitrile, adipodinitrile and hexamethylenediamine, wherein a) the hexamethylenediamine is separated from the mixture to give a mixture (I) with a hexamethylenediamine content of less than 1% by weight;

b) all or part of the 6-aminocapronitrile is separated from the mixture (I) to give a mixture (II) whose content of substances which boil above 6-aminocapronitrile under distillation conditions and cannot be formed by dimerization reactions of 6-aminocapronitrile under thermal stress is less than 1% by weight; and c) all or part of the hexamethylenediamine present is separated from the mixture (II) to give a mixture (IV) whose hexamethylenediamine content is higher than that of the mixture (II), and a mixture (V) whose hexamethylenediamine content is lower than that of the mixture (II).

It is known that 6-aminocapronitrile can be used for the preparation of caprolactam or polyamides. The 6-aminocapronitrile must have a high purity for such purposes.

6-Aminocapronitrile is conventionally prepared by the partial catalytic hydrogenation of adipodinitrile, which can be obtained by the double hydrocyanation of butadiene in the presence of catalysts. This normally gives a mixture containing 6-aminocapronitrile, unreacted adipodinitrile and hexamethylenediamine, optionally together with solvents, substances boiling below hexamethylenediamine, substances boiling above adipodinitrile, and other by-products.

Numerous processes for the separation of 6-aminocapronitrile from such mixtures to give a 6-aminocapronitrile of said high purity are known, for example from WO 96/20931 and WO 97/23454.

The disadvantage of these processes is the high energy expenditure required to recover 6-aminocapronitrile of sufficient purity from the mixture.

It is an object of the present invention to provide a process which makes it possible, in a technically simple and economic manner and avoiding said disadvantages, to recover 6-aminocapronitrile of sufficient purity from mixtures containing 6-aminocapronitrile, adipodinitrile, hexamethylenediamine and optionally solvents and other secondary components.

We have found that this object is achieved by the process defined at the outset.

Processes for the preparation of mixtures containing 6-aminocapronitrile, adipodinitrile, hexamethylenediamine and optionally solvents, substances boiling below hexamethylenediamine, substances boiling above adipodinitrile, and other by-products are known per se.

Thus mixtures containing 6-aminocapronitrile, adipodinitrile and hexamethylenediamine can be obtained by the partial catalytic hydrogenation of adipodinitrile.

Based on the sum of 6-aminocapronitrile, adipodinitrile and hexamethylenediamine, such mixtures conventionally contain from 5 to 90% by weight, preferably from 10 to 80% by weight and particularly preferably from 20 to 70% by weight of 6-aminocapronitrile and from 5 to 90% by weight, preferably from 10 to 80% by weight and particularly preferably from 20 to 70% by weight of hexamethylenediamine, the remainder being unreacted adipodinitrile.

In the light of previous observations, the catalyst used for the hydrogenation is not critical in terms of the process according to the invention. The mixture can be separated from the catalyst after the hydrogenation in a manner known per se, for example by filtration, this being preferred in the case of a suspension hydrogenation, or by removal of the mixture from the reaction vessel to leave the catalyst in the reaction vessel, this being preferred in the case of a fixed bed hydrogenation.

The hydrogenation can advantageously be carried out in the presence of a solvent. Suitable solvents are organic solvents such as alcohols, preferably alkanols and especially $C_1$–$C_4$ alkanols like methanol, ethanol, n-propanol, i-propanol, n-butanol, i-butanol or s-butanol, esters, preferably esters of an alkanecarboxylic acid, especially a $C_1$–$C_4$ alkanecarboxylic acid like formic acid, acetic acid, propionic acid or butyric acid, with an alkanol, especially a $C_1$–$C_4$ alkanol like methanol, ethanol, n-propanol, i-propanol, n-butanol, i-butanol or s-butanol, ethers such as linear or cyclic ethers, for example dimethyl ether, diethyl ether, methyl t-butyl ether or tetrahydrofuran, hydrocarbons such as aliphatic or aromatic hydrocarbons, for example benzene, toluene, ethylbenzene, o-xylene, m-xylene or p-xylene, amines such as primary, secondary or tertiary amines, lactones such as butyrolactone, lactams such as caprolactam, pyrrolidone or N-methylpyrrolidone, and amides, or inorganic solvents such as ammonia, or mixtures thereof.

Preferred solvents are alcohols, especially methanol and ethanol, aromatic hydrocarbons, especially toluene, and ammonia, or mixtures thereof.

If the hydrogenation is carried out in the presence of a solvent, the reaction mixture will then contain this solvent. Prior to the process according to the invention, the solvent can advantageously be separated from the reaction mixture in a manner known per se, for example by distillation or rectification.

This separation can advantageously be performed by fractional distillation in one or more, such as 2 or 3, distillation apparatuses.

Suitable apparatuses are those conventionally used for distillation, for example those described in: Kirk-Othmer, Encyclopedia of Chemical Technology, 3rd ed., vol. 7, John Wiley & Sons, New York, 1979, pages 870–881, such as sieve-plate columns, bubble-cap columns or packed columns, with or without a side discharge.

By-products, for example substances boiling below hexamethylenediamine and/or substances boiling above adipodinitrile, can be formed in the hydrogenation.

In terms of the present invention, substances boiling below hexamethylenediamine are understood as meaning compounds which have a boiling point below that of hexamethylenediamine under the appropriate distillation conditions.

Examples of possible substances boiling below hexamethylenediamine are hexamethyleneimine, hexylamine, aminomethylcyclopentylamine and diaminocyclohexane. Such compounds are present in the mixtures obtained from the hydrogenation in overall amounts of up to 10% by weight, preferably of up to 5% by weight, based on the sum of 6-aminocapronitrile, adipodinitrile and hexamethylenediamine.

Prior to the process according to the invention, substances boiling below hexamethylenediamine can advantageously be separated from the reaction mixture in a manner known per se, for example by distillation or rectification.

This separation can advantageously be performed by fractional distillation in one or more, such as 2 or 3, distillation apparatuses.

Suitable apparatuses are those conventionally used for distillation, for example those described in: Kirk-Othmer, Encyclopedia of Chemical Technology, 3rd ed., vol. 7, John Wiley & Sons, New York, 1979, pages 870–881, such as sieve-plate columns, bubble-cap columns or packed columns, with or without a side discharge.

Any solvent used and any substances present which boil below hexamethylenediamine can be separated off simultaneously in step a or beforehand. Preferably, any solvent used is separated off first (step a0), followed by any substances present which boil below hexamethylenediamine (step a1).

Step a1 should advantageously be carried out at a pressure below ambient atmospheric pressure, preferably at an absolute pressure below 500 mbar.

According to the invention, hexamethylenediamine is separated from the mixture in step a to give a mixture (I) with a hexamethylenediamine content below 5% by weight, preferably below 1% by weight, based on the mixture (I).

This separation can advantageously be performed by fractional distillation in one or more, such as 2 or 3, distillation apparatuses.

Suitable apparatuses are those conventionally used for distillation, for example those described in: Kirk-Othmer, Encyclopedia of Chemical Technology, 3rd ed., vol. 7, John Wiley & Sons, New York, 1979, pages 870–881, such as sieve-plate columns, bubble-cap columns or packed columns, with or without a side discharge, preferably with a side discharge.

Step a should advantageously be carried out at a pressure below ambient atmospheric pressure, preferably at an absolute pressure below 500 mbar.

In one preferred embodiment, hexamethylenediamine and components boiling below hexamethylenediamine can be separated off together, i.e. steps a1 and a can be carried out together.

In this operation, hexamethylenediamine can advantageously be recovered at a side discharge.

In one particularly preferred embodiment, the column used has a separating plate in the region between the feed and the side discharge.

According to the invention, all or part of the 6-aminocapronitrile is separated from the mixture (I) in step b to give a mixture (II) whose content of substances which boil above 6-aminocapronitrile under distillation conditions and cannot be formed by dimerization reactions of 6-aminocapronitrile under thermal stress is less than 2% by weight, preferably less than 0.1% by weight.

This separation can advantageously be performed by fractional distillation in one or more, such as 2 or 3, distillation apparatuses.

Suitable apparatuses are those conventionally used for distillation, for example those described in: Kirk-Othmer, Encyclopedia of Chemical Technology, 3rd ed., vol. 7, John Wiley & Sons, New York, 1979, pages 870–881, such as sieve-plate columns, bubble-cap columns or packed columns, with or without a side discharge, preferably with a side discharge.

Step b should advantageously be carried out at a pressure below ambient atmospheric pressure, preferably at an absolute pressure below 500 mbar.

According to the invention, all or part of the hexamethylenediamine present is separated from the mixture (II) in step c to give a mixture (IV) whose hexamethylenediamine content is higher than that of the mixture (II), and a mixture (V) whose hexamethylenediamine content is lower than that of the mixture (II).

This separation can advantageously be performed by fractional distillation in one or more, such as 2 or 3, distillation apparatuses.

Suitable apparatuses are those conventionally used for distillation, for example those described in: Kirk-Othmer, Encyclopedia of Chemical Technology, 3rd ed., vol. 7, John Wiley & Sons, New York, 1979, pages 870–881, such as sieve-plate columns, bubble-cap columns or packed columns, with or without a side discharge.

Step c should advantageously be carried out at a pressure below ambient atmospheric pressure, preferably at an absolute pressure below 500 mbar.

In one preferred embodiment, the pressure in step a should be lower than the pressure in step c.

In another preferred embodiment, the mixture (IV) obtained in step c can be recycled into step a, the mixture (IV) preferably being vaporous.

In another embodiment of step b in terms of the present invention, it is possible to allow a higher content of substances boiling above 6-aminocapronitrile to give a mixture (IIa) and separate components boiling above 6-aminocapronitrile from the mixture (IIa) to give a mixture (VI) whose 6-aminocapronitrile content is higher than that of the mixture (II), and a mixture (VII) whose 6-aminocapronitrile content is lower than that of the mixture (II).

In another preferred embodiment, the mixture (VII) can be recycled into step b.

The hexamethylenediamine content of the mixture (V) should advantageously be at most 5000 ppm, preferably 0 to 1000 ppm and particularly preferably 0 to 200 ppm, based on the weight of the mixture (V). The sum of the components of the mixture (V) other than 6-aminocapronitrile should advantageously be at most 5000 ppm, preferably 0 to 500 ppm and particularly preferably 0 to 200 ppm, based on the weight of the mixture (V).

The total energy consumption of the process according to the invention, calculated as the sum of the energy consumptions in steps a, b and c, and optionally a0 and a1, is lower than the energy consumption required when the separation is carried out in only two steps a and c, and optionally a0 and a1, to achieve the same hexamethylenediamine content in the 6-aminocapronitrile separated off.

DETAILED DESCRIPTION OF THE DRAWINGS

Figure 1:
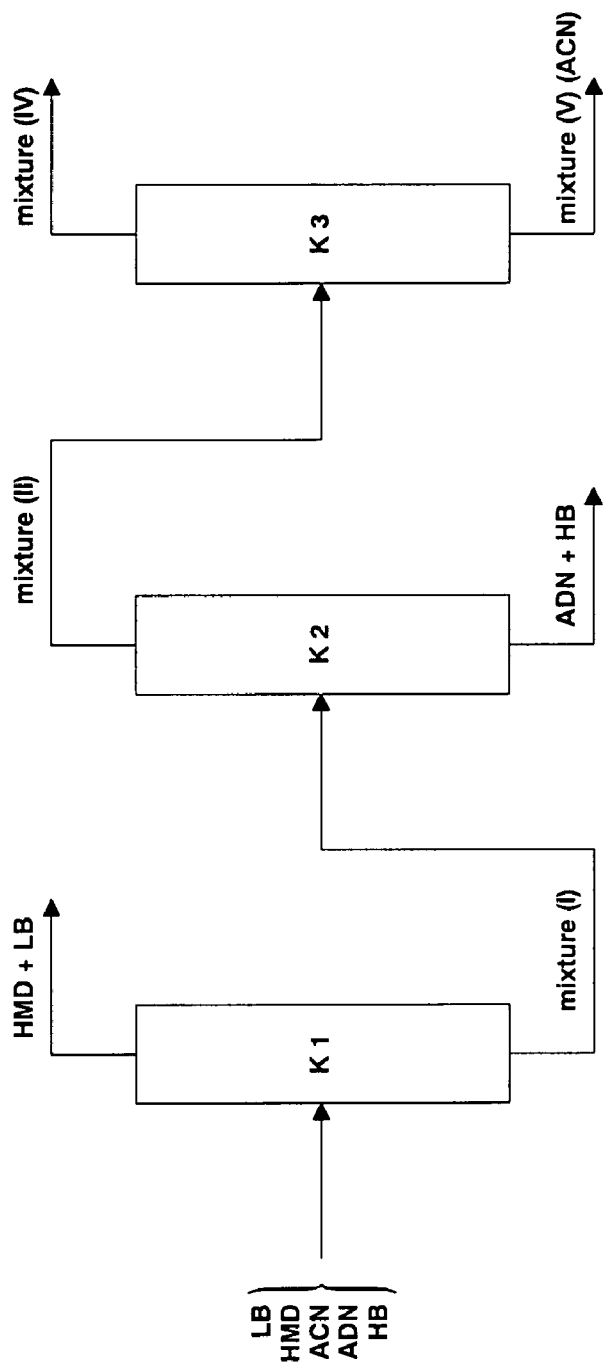
FIGS. 1 to 3 schematically illustrate the separation of a raw mixture comprising 6-aminocapronitrile (ACN), adipodinitrile (ADN) and hexamethylenediamine (HMD), as well as substances boiling above adipodinitrile (HB) and substances boiling below hexamethylenediamine (LB).

In the embodiment of the process which is illustrated in FIG. 1, the raw mixture comprising 6-aminocapronitrile (ACN), adipodinitrile (ADN) and hexamethylenediamine (HMD), as well as substances boiling above adipodinitrile (HB) and substances boiling below hexamethylenediamine (LB) is separated in a distillation column (K1) into a hexamethylenediamine (HMD) fraction which comprises substances boiling below hexamethylenediamine (LB), and a mixture (I) which comprises 6-aminocapronitrile and adipodinitrile and has a hexamethylenediamine content of less than 1% by weight. The mixture (I) is conveyed into a distillation column (K2) and is separated into an adipodinitrile fraction which also comprises substances boiling above adipodinitrile (HB) and a mixture (II) which comprises 6-aminocapronitrile and which contains less than 1% by weight of substances which boil above 6-aminocapronitrile under distillation conditions and which cannot be formed by dimerization reactions of 6-aminocapronitrile under thermal stress. The mixture (II) is conveyed into a distillation column (K3) where it is separated into a mixture (IV) which has a higher hexamethylenediamine content than the mixture (II), and 6-aminocapronitrile (mixture (V)) which has a lower hexamethylenediamine content than the mixture (II).

Figure 2:
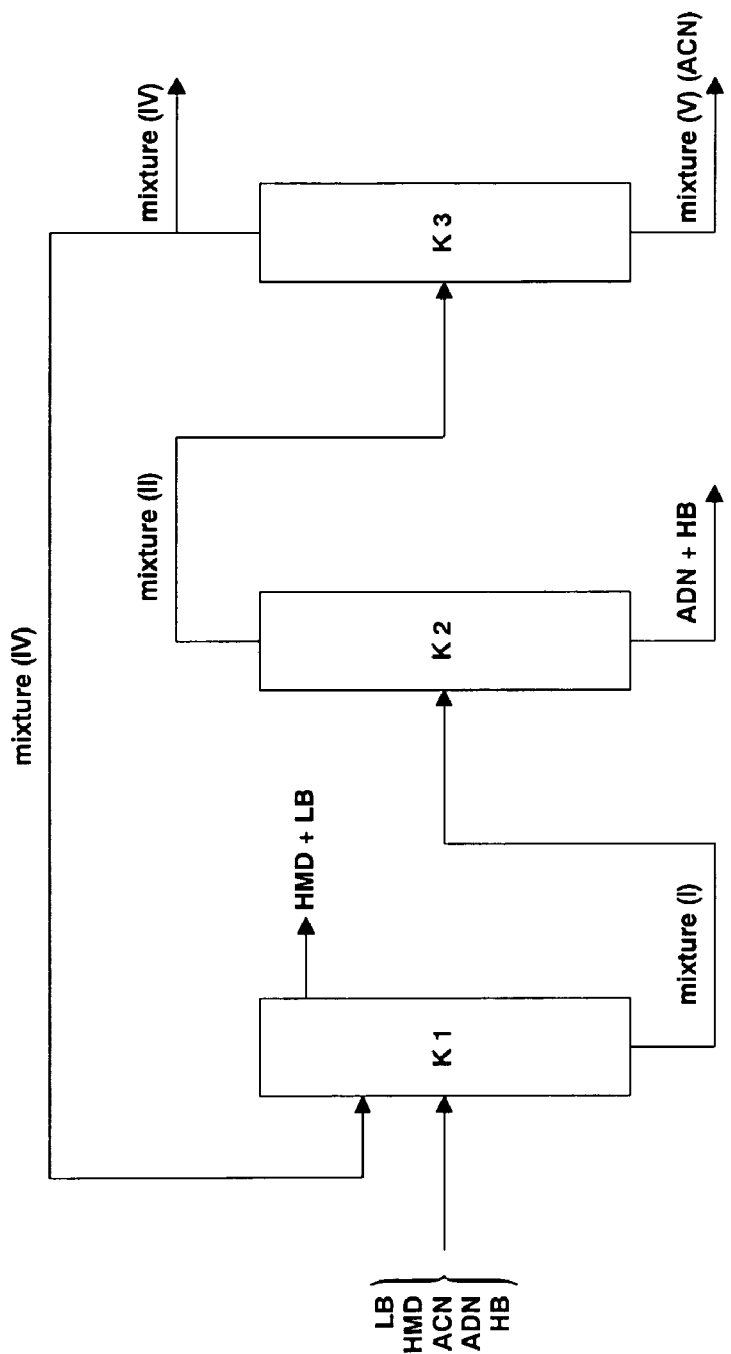

The embodiment of the process which is illustrated in FIG. 2 essentially corresponds to the embodiment of the process which is illustrated in FIG. 1. FIG. 2 additionally illustrates that the hexamethylenediamine (HMD) fraction which comprises substances boiling below hexamethylenediamine (LB) can be removed from the distillation column (K1) at a side discharge, and that a part of the mixture (IV) which is separated off in column (K3) can be recycled into the column (K1).

Figure 3:
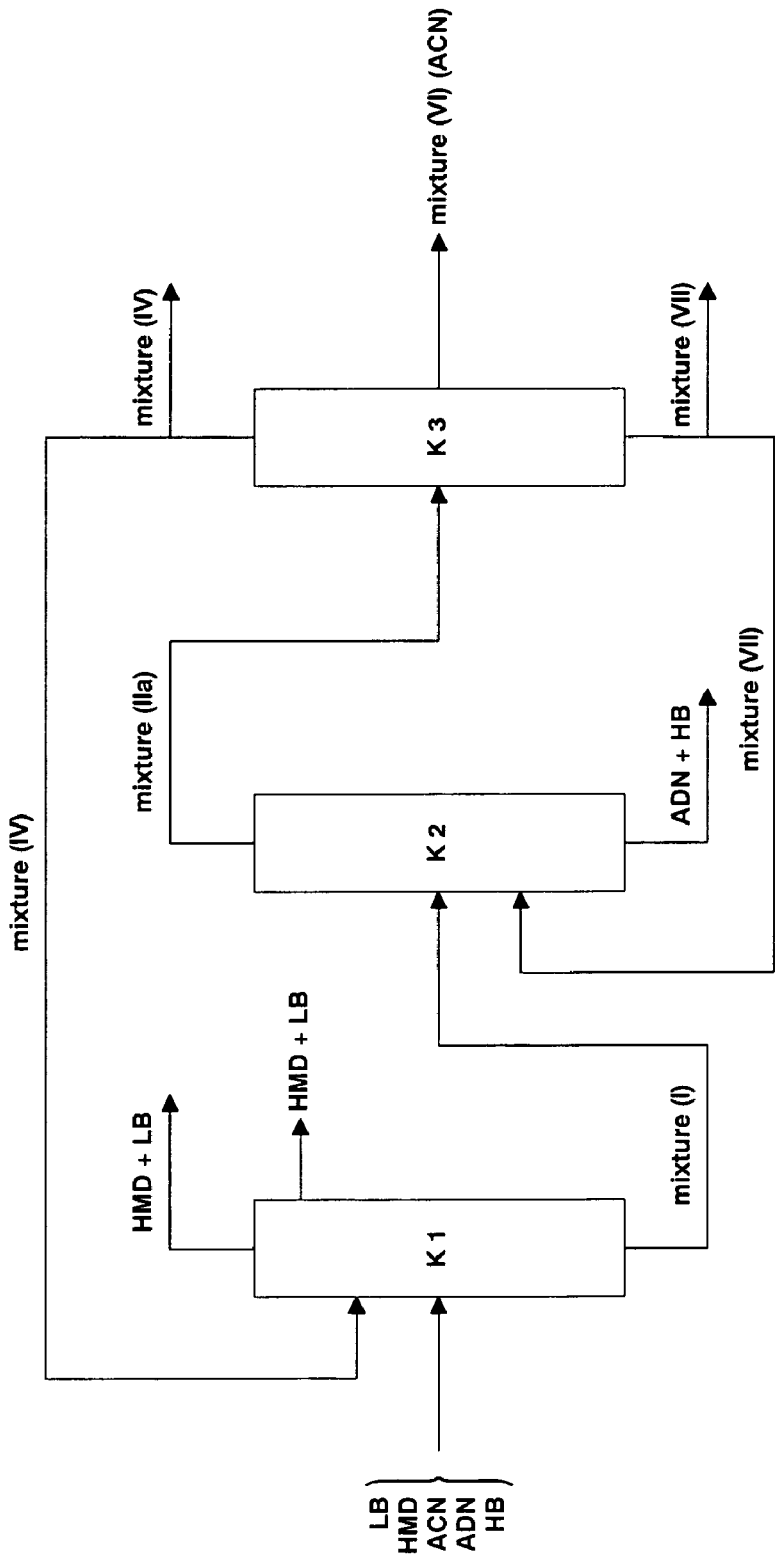

In the embodiment of the process which is illustrated in FIG. 3, the separation of the mixture (I) in the distillation column (K2) is conducted such that a mixture (IIa) is separated off which has a higher content of components boiling above 6-aminocapronitrile than the mixture (II). The mixture (IIa) is then conveyed into the distillation column (K3) where it is separated into a mixture (IV) which has a higher hexamethylenediamine content than the mixture (II), a mixture (VI) which has a higher 6-aminocapronitrile content than the mixture (II), and a mixture (VII) which has a lower 6-aminocapronitrile content than the mixture (II). In accordance with this embodiment, a part or all of the mixture (VII) can be recycled into the column (K2).

EXAMPLE

In a distillation column K1, 200 kg/h of a hydrogenation mixture containing 29% of hexamethylenediamine, 42% of 6-aminocapronitrile, 27% of adipodinitrile, 0.5% of low-boiling components and 1.5% of high-boiling components were separated off so that 1.5 kg/h containing essentially low-boiling components were withdrawn at the top.

58 kg/h of hexamethylenediamine with a 6-aminocapronitrile content of 110 ppm were withdrawn at a side discharge. 156.5 kg/h with a hexamethylenediamine content of 0.2% were withdrawn at the bottom of the column K1. Said column was operated with 90 kg/h of steam. In a second distillation column K2, the bottom product withdrawn from column K1 was distilled so that 116.5 kg/h of 6-aminocapronitrile with a hexamethylenediamine content of 0.3% were withdrawn at the top. 58 kg/h with a 6-aminocapronitrile content of 2% were withdrawn at the bottom. The top product of column K2 was distilled in a third column K3 so that 17 kg/h of vapor were withdrawn at the top and recycled into column K1. Column K2 was operated with 30 kg/h of steam. 99.5 kg/h of 6-aminocapronitrile with a hexamethylenediamine content of 45 ppm were withdrawn from column K3 at a side discharge. Column K3 was operated with 5 kg/h of steam. The steam consumption of columns K1+K3 was 95 kg/h.

COMPARATIVE EXAMPLE

In distillation column K1 according to the Example, 200 kg/h of a hydrogenation mixture containing 29% of hexamethylenediamine, 42% of 6-aminocapronitrile, 27% of adipodinitrile, 0.5% of low-boiling components and 1.5% of high-boiling components were separated off so that 1.5 kg/h containing essentially low-boiling components were withdrawn at the top.

58 kg/h of hexamethylenediamine with a 6-aminocapronitrile content of 115 ppm were withdrawn at a side discharge. 156.5 kg/h with a hexamethylenediamine content of 0.05% were withdrawn at the bottom of column K1. 140 kg/h of steam were necessary to obtain this hexamethylenediamine content at the bottom of the column. In a second distillation column K2, the bottom product withdrawn from column K1 was distilled so that 116.5 kg/h of 6-aminocapronitrile were withdrawn at the top. The hexamethylenediamine content of the top discharge was 800 ppm. The column was operated with 30 kg/h of steam.

Despite the fact that the energy consumption of column K1 in the Comparative Example (140 kg/h) was higher than the sum of the energy consumptions in columns K1 and K3 in the Example (95 kg/h overall), the ACN purity achieved was markedly poorer in the Comparative Example.

We claim:

1. A process for the distillative separation of 6-aminocapronitrile from a raw mixture containing 6-aminocapronitrile, adipodinitrile and hexamethylenediamine, wherein
    a) the raw mixture is separated into a hexamethylenediamine fraction and a mixture (I) which comprises 6-aminocapronitrile and adipodinitrile and has a hexamethylenediamine content of less than 1% by weight;
    b) all or part of the 6-aminocapronitrile is separated from the mixture (I) to give an adipodinitrile fraction and a mixture (II) which comprises 6-aminocapronitrile and which contains less than 1% by weight of substances which boil above 6-aminocapronitrile under distillation conditions and which cannot be formed by dimerization reactions of 6-aminocapronitrile under thermal stress; and
    c) the mixture (II) is separated into a mixture (IV) which has a higher hexamethylenediamine content than the mixture (II), and 6-aminocapronitrile (mixture (V)) which has a lower hexamethylenediamine content than the mixture (II).

2. A process as claimed in claim 1 wherein the hexamethylenediamine fraction is recovered from the separation in step (a) at a side discharge.

3. A process as claimed in claim 1 wherein the hexamethylenediamine fraction which is separated off from the raw mixture in step (a) comprises components boiling below hexamethylenediamine.

4. A process as claimed in claim 1 wherein all or part of the mixture (IV) which is separated off in step (c) is recycled into step (a).

5. A process as claimed in claim 4 wherein the mixture (IV) which is recycled from step (c) into step (a) is vaporous.

6. A process as claimed in claim 1 wherein the pressure in step (b) is chosen so that the bottom temperature does not exceed 185° C.

7. A process for the distillative separation of 6-aminocapronitrile from a raw mixture containing 6-aminocapronitrile, adipodinitrile and hexamethylenediamine, wherein
    a) the raw mixture is separated into a hexamethylenediamine fraction and a mixture (I) which comprises 6-aminocapronitrile and adipodinitrile and has a hexamethylenediamine content of less than 1% by weight;
    b) all or part of the 6-aminocapronitrile is separated from the mixture (I) to give an adipodinitrile fraction and a mixture (IIa) which comprises 6-aminocapronitrile; and
    c) the mixture (IIa) is separated into a mixture (IV) which has a higher hexamethylenediamine content than the mixture (IIa), aminocapronitrile (mixture (VI)) which has a higher 6-aminocapronitrile content than the mixture (IIa), and a mixture (VII)) which has a lower 6-aminocapronitrile content than the mixture (IIa).

8. A process as claimed in claim 7 wherein all or part of the mixture (VII) is recycled into step (b).

* * * * *